United States Patent [19]
Dozol et al.

[11] Patent Number: 5,607,591
[45] Date of Patent: Mar. 4, 1997

[54] BIS-CROWN CALIX [4]ARENES, THEIR PREPARATION PROCESS AND THEIR USE FOR THE SELECTIVE EXTRACTION OF CESIUM AND ACTINIDES

[75] Inventors: Jean-François Dozol, Peneverg; Zouhair Asfari, Strasbourg; Clément Hill, Obernai; Jacques Vicens, Strasbourg, all of France

[73] Assignee: Commissariat A L'Energie Atomique, Paris, France

[21] Appl. No.: 436,287

[22] PCT Filed: Nov. 25, 1993

[86] PCT No.: PCT/FR93/01161
§ 371 Date: May 17, 1995
§ 102(e) Date: May 17, 1995

[87] PCT Pub. No.: WO94/12502
PCT Pub. Date: Jun. 9, 1994

[30] Foreign Application Priority Data

Nov. 26, 1992 [FR] France .................. 92 14245

[51] Int. Cl.⁶ .................................. B01D 61/38
[52] U.S. Cl. .................. 210/638; 210/643; 423/9
[58] Field of Search ....................... 210/643, 634, 210/638; 423/9; 252/625

[56] References Cited

U.S. PATENT DOCUMENTS 4,477,377 10/1984 Izatt et al. .................. 252/631
4,906,376 3/1990 Fyles .................. 210/506 X

OTHER PUBLICATIONS

Journal of the American Chemical Society, vol. 112, No. 19, 12 Sep. 1990, Gaston, PA, U.S., pp. 6979–6985, Eleonora Ghidini et al.: Complexation of Alkali Metal Cations by Conformationally Rigid, Stereoisomeric Calix[4]Arene Crown Ethers: A Quantitative evaluation of Preorganization.

*Primary Examiner*—Frank Spear
*Attorney, Agent, or Firm*—Pearne, Gordon, McCoy & Granger

[57] ABSTRACT

The invention relates to bis-crown calix[4]arenes, their preparation process and their use for the selective extraction of cesium and actinides. Bis-crown calix[4]arenes are in accordance with the formula:

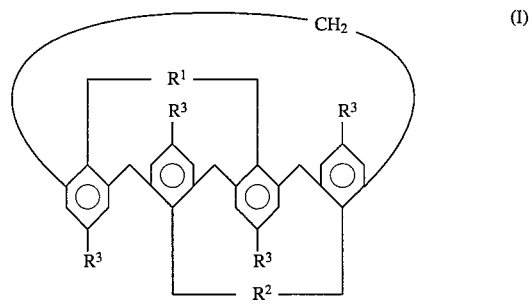

in which $R^1$ and $R^2$ respectively represent $X(C_2H_4X)_m$ and $X(C_2H_4X)_n$ with $X=O$, NH and/or $N(CH_3)$, m and n=3, 4, 5 or 6, or $X(C_2H_4X)_{p/2}XY(C_2H_4X)_{p/2}$ with p=2 or 4 and Y=cycloalkylene or arylene. These bis-crown calix[4]arenes, whose benzene nuclei are optionally substituted by alkyl groups, can be used as an extracant, e.g. in the form of a liquid membrane, for separating cesium from acid solutions containing sodium in a large quantity compared with the cesium quantity, e.g. effluents of irradiated fuel reprocessing plants.

11 Claims, 1 Drawing Sheet

1,3-BIS- CROWN-5-
p-ISOPROPYL CALIX (4) ARENE

FIG. 1
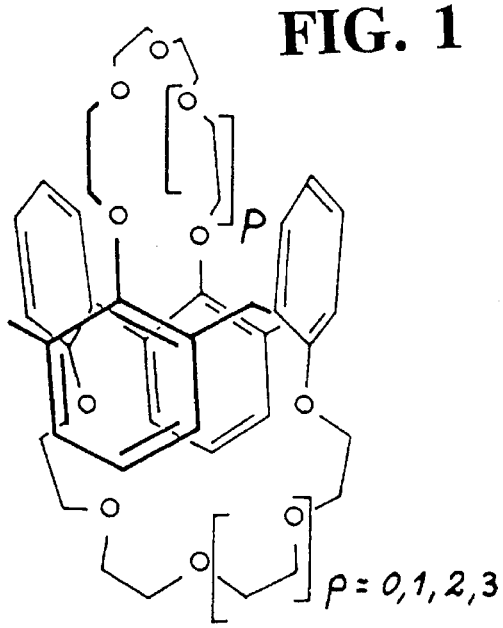
1,3-BIS-CROWN-n-CALIX (4) ARENE
FIG. 2
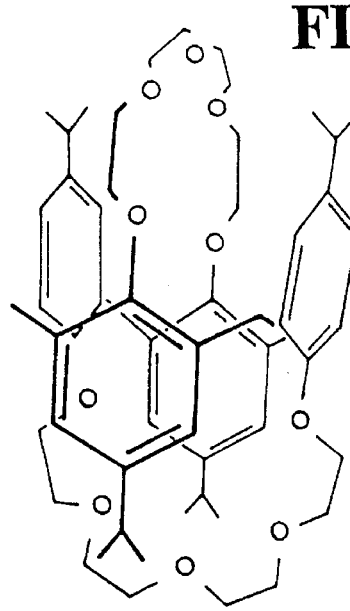
1,3-BIS-CROWN-5-p-ISOPROPYL CALIX (4) ARENE
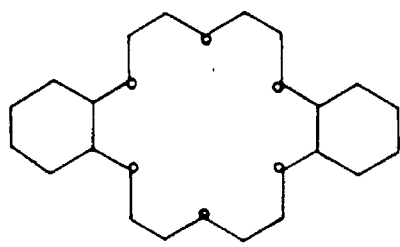
DCH18C6
FIG. 3
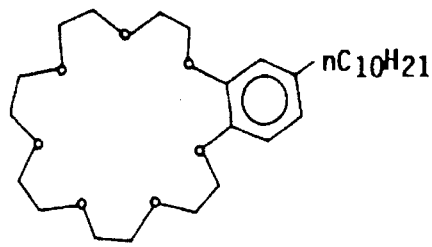
n DECYL-B21C7
FIG. 4
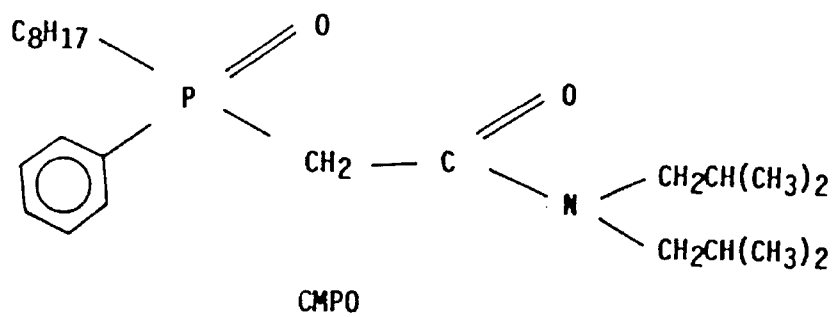
CMPO
FIG. 5

BIS-CROWN CALIX [4]ARENES, THEIR PREPARATION PROCESS AND THEIR USE FOR THE SELECTIVE EXTRACTION OF CESIUM AND ACTINIDES

The present invention relates to bis-crown calix[4]arenes, their preparation process and their use for the selective extraction of cesium and actinides.

More specifically, it relates to bis-crown calix[4]arenes able to selectively extract the cesium and actinides present in the state of traces in acid solutions which may or may not have high cation concentrations, such as aqueous effluents from irradiated nuclear fuel reprocessing installations or irradiated fuel dissolving solutions. In such effluents, cesium 137 is one of the most noxious fission products as a result of its long half-life (thirty years). It is therefore of interest to selectively eliminate it from the liquid effluents from reprocessing plants, particularly the concentrates of evaporators and acid solutions which may or may not have a high salinity due to the presence of sodium nitrate.

In view of the very similar chemical properties of sodium and cesium, it is extremely difficult to selectively extract the cesium present in these effluents, at a concentration generally below $10^{-6}$ mole/l, whereas the sodium concentration is approximately 4 mole/l. In order to solve this problem consideration has been given to the extraction of cesium by means of macrocyclic ligands such as para-tert.-butyl calixarenes, as described in U.S. Pat. No. 4,477,377. The para-tert.-butyl calixarenes used are the tetramer, hexamer and oxtamer and the best results are obtained with the hexamer and octamer, the tetramer not having a very good selectivity for separating cesium from potassium. This cesium extraction procedure is of interest, but suffers from the main disadvantage of only being applicable to the treatment of basic aqueous solutions, whereas most effluents resulting from reprocessing are acid solutions.

Other macrocyclic ligands such as crown ethers have also been used for this purpose, as is described by Dozol et al in report EUR 13887 FR of the Commission of the European Union (1992), but they have a low selectivity with respect to cesium.

The present invention isdirected at novel calixarenes making it possible to selectively extract cesium from acid solutions and separate it from sodium with a good efficiency.

According to the invention, the calixarenes are bis-crown calix[4]arenes of formula:

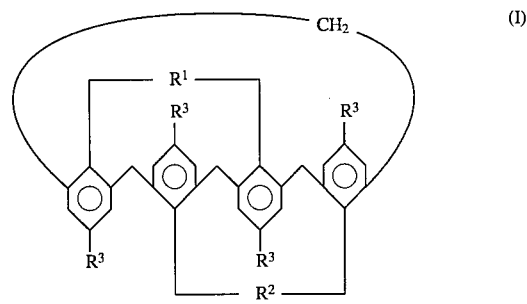

in which
 $R^1$ represents X $(C_2H_4X)_m$ with X representing O, NH and/or N $(CH_3)$ and m being equal to 3, 4, 5 or 6,
 $R^2$ represents X $(C_2H_4X)_n$ with X representing O, NH and/or N$(CH_3)$ and n being equal to 3, 4, 5 or 6, or
 $R^1$ and $R^2$ represent X $(C_2H_4X)_{p/2}$ YX $(C_2H_4X)_{p/2}$ with X representing O, NH and/or N$(CH_3)$, p being equal to 2 or 4 and Y representing a cycloalkylene or arylene group and
 $R^3$ represents a hydrogen atom or a $C_1$ to $C_3$ alkyl group.

In the above formula, the term "cycloalkylene" group is understood to mean a divalent group derived from a cyclic hydrocarbon by removing a hydrogen atom from each of the two carbon atoms of the cycle. As an example of such a group reference can be made to the cyclohexylene group.

The term "arylene" group is understood to mean a divalent group derived from an aromatic or heterocyclic nucleus by removing a hydrogen atom from each of the two carbon atoms of the cycle. Examples of such groups are phenylene, naphthylene, pyridylene and thiophenylene groups.

In the $R^1$ and/or $R^2$ links, the X can represent hydrogen atoms, which can be partly or totally replaced by NH or N$(CH_3)$. Generally m and n are identical and are preferably equal to 4 or 5.

These calixarenes are very different from the calixarenes used in U.S. Pat. No. 4,477,377. Thus, in the latter document, use was made of calixarenes having on each benzene nucleus a phenol group or a tert.-butyl group, said calixarenes only having a single macrocycle.

However, in the case of the calixarenes according to the invention, there are three cycles respectively constituted by a first cycle corresponding to all the benzene nuclei linked by $CH_2$ groups, a second cycle formed by a crown ether bridge between the benzene nuclei in the 1 and 3 positions and a third cycle of the crown ether type between the benzene nuclei in the 2 and 4 positions.

As a result of this special structure, these calixarenes combine the complexing properties of crown ethers with respect to alkalis with the properties of calixarenes, i.e. a high selectivity imposed by the rigid structure of the cavity and a high lipophilic character making the molecule of particular interest for use in a supported liquid membrane.

The calixarenes of the invention can be prepared by a process consisting of reacting a calix[4]arene of formula:

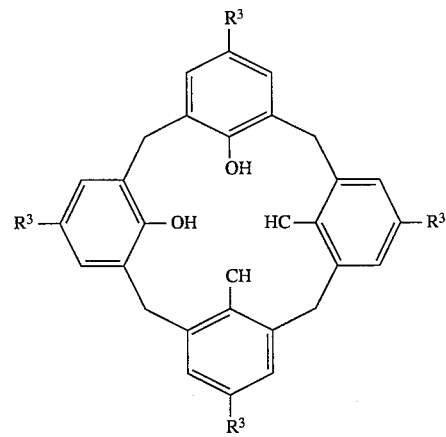

in which $R^1$ has the meaning given hereinbefore,
with a tetra, penta or hexa ethylene glycol of formula:

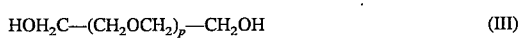

$$HOH_2C—(CH_2OCH_2)_p—CH_2OH \quad (III)$$

in which p=2, 3, 4 or 5, or
with two different glycols of formula (III), or
with a glycol of formula

$$[HOCH_2(CH_2OCH_2)_2O]_2—Y \quad (IV)$$

in which Y has the meaning given hereinbefore.

For this reaction, the glycols of formula (III) or (IV) are transformed into diparatoluene sulphonates.

In order to perform this reaction, the calixarene is dissolved in an appropriate solvent, e.g. acetonitrile, to it is added a salt such as potassium carbonate and stirring is maintained for at least 20 minutes at ambient temperature. This is followed by the addition of the tetra, penta or hexa ethylene glycol of formula III or the glycol of formula IV in the form of diparatoluene sulphonate and it is allowed to react at reflux for an adequate time (at least 8 days) to form a crown ether bridge linking two opposite benzene nuclei. This is followed by the addition of a new quantity of tetra, penta or hexa ethylene glycol in the forms described hereinbefore in order to form the second crown ether bridge. After the reaction, the reaction mixture is dissolved in an appropriate solvent and the calixarene is extracted, e.g. using hydrochloric acid.

Bis-crown calix[4]arenes of formula

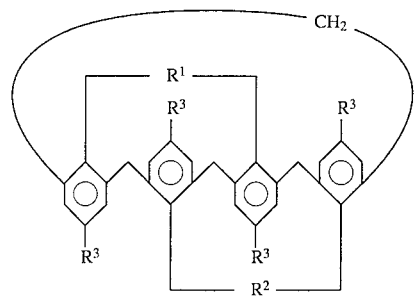

which $R^1$ represents $X(C_2H_4X)_m$ with X representing O, NH and/or N (CH3) and m being equal to 3, 4, 5 or 6, $R^2$ represents $X(C_2H_4X)$ n with X representing O, NH and/or $N(CH_3)$ and n being equal to 3, 4, 5 or 6, or $R^1$ and $R^2$ represent $X(C_2H_4X)_{p/2}YX(C_2H_4X)_{p/2}$ with X representing O, NH and/or $N(CH_3)$, p being equal to 2 or 4 and Y representing a cycloalkylene or arylene group and $R^3$ represents a hydrogen atom or a $C_1$ to $C_3$ alkyl group, can in particular be used for the selective extraction of the cesium present in aqueous solutions, particularly acid solutions which may or may not contain sodium, such as dissolving solutions and aqueous effluents from irradiated fuel reprocessing installations.

When the bis-crown calix[4]arene used has alkyl substituents on the benzene nuclei, it can be prepared by a process identical to that described hereinbefore starting with the corresponding substituted calix[4]arene.

A substituted bis-crown calix[4]arene of this type with $R^3$ representing the tert.-butyl group is described by Ghidini et al in J. Am. Chem. Soc., 1990, 112, pp. 6979–6985, but it is obtained as a secondary product with a very low yield, also using a reagent, potassium tert.-butylate, which is flammable and dangerous, and a benzene solvent not usable in industry.

For the extraction of the cesium, the aqueous starting solutions can be acid solutions, e.g. nitric solutions containing $10^{-3}$ to 7 mole/l of nitric acid.

In order to carry out this extraction, the aqueous solution containing the cesium is contacted with an immiscible liquid phase including the bis-crown calix[4]arene and then the extracted cesium is recovered in the immiscible liquid phase.

This recovery can be performed by means of an aqueous solution by contacting the immiscible liquid phase having extracted the cesium with an aqueous reextraction solution, e.g. constituted by distilled, deionized water.

In order to perform this process, the contacting of the aqueous solution and the immiscible liquid phase takes place in conventional liquid—liquid extraction installations such as mixer-settlers, exchange columns, etc.

This contacting can also be brought about by disposing the immiscible liquid phase including the bis-crown calix [4]arene in the form of a liquid membrane having two opposite surfaces, making the aqueous starting solution containing the cesium circulate on one of the surfaces of the membrane and collecting the cesium extracted by the liquid membrane in an aqueous reextraction solution circulating on the opposite surface of the membrane.

To form the immiscible liquid phase, the bis-crown calix [4]arene is dissolved in an appropriate solvent.

Examples of usable solvents are alkyl benzenes and nitrophenyl alkyl ethers.

The preferred solvent is an ether such as orthonitrophenyl hexyl ether and ortho-nitrophenyl octyl ether.

The bis-crown calix[4]arene concentration of the immiscible liquid phase is in particular dependent on the solvent used. It is possible to use concentrations from $10^{-4}$ to $5 \cdot 10^{-2}$ mole/l, e.g. a concentration of $10^{-2}$ mole/l.

The bis-crown calix[4]arenes of formula (IV) can also be used for separating certain actinides from trivalent americium. In this case, contacting also takes place of the aqueous solution containing the actinides with an immiscible liquid phase containing the bis-crown calix[4]arene in order to selectively extract the actinides, while keeping the americium in the aqueous solution.

It is pointed out that for the extraction of cesium and also actinides, it is possible to use the calixarenes in the form of pure isomers or isomer mixtures. It is also possible to use mixtures of calixarenes.

BRIEF DESCRIPTION OF THE DRAWINGS

Other features and advantages of the invention can be better gathered from the following examples given in illustrative and non-limitative manner with reference to the attached drawing, which Shows the different ligands used in these examples.

FIG. 1 represents the structural formula of 1,3-bis-crown-5-calix[4]arene of example 1;

FIG. 2 represents the structural formula of 1,3-bis-crown-5-p-isopropyl calix[4]arene used in example 30;

FIG. 3 represents the structural formula of dicyclohexano-18-crown-6-ether (OCH18C6) of example 20;

FIG. 4 represents the structural formula of decylbenzo-21-crown-7-ether of example 26; and FIG. 5 represents the structural formula of CMPO of example 33.

DETAILED DESCRIPTION OF THE EXAMPLES

EXAMPLE 1

Preparation of 1,3-bis-crown-5-calix[4]arene

Into a 1 liter flask equipped with a condenser are introduced 700 ml of acetonitrile, 6.00 g (14.2 mmole) of calix[4]arene and 19.62 g (142 mmole) of potassium carbonate. The mixture is stirred at ambient temperature for 20 min. followed by the addition thereto of 7.14 g (14.2 mmole) of tetraethylene glycol-di-p-toluene sulphonate and refluxing takes place under nitrogen.

After 8 days addition takes place of the same quantities of tetraethylene glycol-di-p-toluene sulphonate, namely 7.12 g (14.2 mmole) and potassium carbonate, i.e. 19.62 g (142 mmole) and the reaction mixture is left at reflux for 10 days.

After cooling the reaction mixture, it is filtered, washed with dichloromethane and evaporated on the rotary evaporator. The product is then dissolved in dichloromethane and the thus obtained organic solution is extracted with a 1N hydrochloric acid (HCl) solution. The filtrate is concentrated on the rotary evaporator and the constituents are separated from the oil obtained on a silica column using as the eluent a dichloromethane—acetone mixture (85:15 by volume). The sought product is eluted and is then precipitated in methanol.

This gives 1.145 g of 1,3-bis-crown-5-calix [4]arene, which corresponds to a 10% yield.

This product has the following characteristics:

melting point: 117°–118° C.

NMR of the proton in CDCl$_3$: 7.09 ppm (d, 8H, J=7.5 Hz,—Ar—Hmeta), 6.89 ppm (t, 4H, J=7.5 Hz, Ar—Hpara), 3.88 ppm (s, 8H,Ar—C$\underline{h}_2$—Ar), 3.59–3.06 ppm (m, 32H, O—CH—C$\underline{H}_2$C$\underline{H}_2$—O). FAB :m/z=740.3 elementary analysis:

calculated for C$_{44}$H$_{52}$O$_{10}$ CH$_3$ OH: C=70.02%; H=7.18%, found: C70.23%; H=6.92%.

EXAMPLE 2

Preparation of the 1,3-bis-5-crown-calix[4]arene cesium complex 53 mg (7.16·10$^{-2}$ mmole) of the 1,3-bis-crown-5-calix[4] arene obtained in example 1 are dissolved in 3 ml of chloroform. After stirring the mixture a cesium picrate excess is added. After 24 h, the reaction mixture is filtered and the filtrate concentrated in the rotary evaporator. This gives 62 mg of complex in the solid state, which corresponds to a 99% yield.

The characteristics of the complex are as follows:

melting point: 73°–74° C.

NMR of the proton in CDCl$_3$: 8.87 ppm (s, 2H, Ar—$\underline{H}$, picrate) 7.3 ppm (d, 8H, J=7.28 Hz, Ar—$\underline{H}$meta) 6.94 ppm (m, 4H, Ar—$\underline{H}$, para) 3.94 ppm–3.24 ppm (m, 40H, Ar—C$\underline{H}_2$Ar+O—C$\underline{H}_2$—C$\underline{H}_2$—O). FAB: m/z (=873.1).

EXAMPLE 3

Preparation of 1,3-bis-crown-6-calix[4]arene 100 ml of acetonitrile, 850 mg (2 mmole) of calix[4]arene and 2.764 g (20 mmole) of potassium carbonate are kept under stirring at ambient temperature in a 250 ml flask. This is followed by the addition of 1.14 g (2 mmole) of pentaethylene glycol-di-p-toluene sulphonate and reflux is maintained for 8 days. This is followed by the addition of the same quantities of pentaethylene glycol-di-p-toluene sulphonate and potassium carbonate and reflux is maintained for 10 days. The reaction mixture is then concentrated with the rotary evaporator, the solid obtained is dissolved in dichoromethane and then extraction takes place with 1N hydrochloric acid (HCl). The organic solution is dried on sodium sulphate and concentrated with the rotary evaporator. The resulting oil is precipitated in ether, which gives 662 mg of 1,3-bis-crown-6-calix[4]arene, which corresponds to a 40% yield.

The product obtained has the following characteristics:

melting point: 145°–146° C.

NMR of proton in CDCl$_3$: 7.10 ppm (d, 8H, J=8 Hz, Ar—$\underline{H}$meta)6.87 ppm (t, 4H, J=8 Hz, Ar—$\underline{H}$para) 3.87 ppm (s, 8H, Ar—C$\underline{H}_2$—Ar) 3.70–3.28 ppm (m, 40H, O—C$\underline{H}_2$—CH$_2$—O). FAB m/z=828.4.

EXAMPLE 4

Preparation of the 1,3-bis-6-crown-6-calix[4]arene cesium complex 52 mg (6.27·10$^{-2}$ mmole) of the 1,3-bis-crown-6-calix[4] arene obtained in example 3 are dissolved in 3 ml of chloroform, followed by the addition of a cesium picrate excess and stirring thereof is maintained for 24 h. The solution is then filtered and the filtrate concentrated with the rotary evaporator, which gives 74 mg of complex in the solid state, i.e. a 99% yield.

The complex has the following characteristics:

melting point: 79°–80° C.

NMR of proton in CDCl$_3$: 8.87 ppm (s, 2H, Ar—H, picrate) 7.27–7.22 ppm (m, 8H, Ar—$\underline{H}$, meta) 7.06–6.98 ppm (m, 4H, Ar—$\underline{H}$, para)3.87–3.58 ppm (m, 48H, ARC$\underline{H}_2$—Ar+O—C$\underline{H}_2$—C$\underline{H}_2$—O). FAB m/z=961.3.

EXAMPLE 5

Preparation of 1,3,-bis-crown-7-calix[4]arene

The same operating procedure as in example 1 is used for preparing 1,3-bis-crown-7-calix[4]arene replacing the tetraethylene glycol-di-p-toluene sulphonate by hexaethylene glycol-di-p-toluene sulphonate. This gives 1,3-bis-crown-7-calix[4]arene with an 18% yield.

This product has the following characteristics:

melting point: 120°–121° C.

NMR of proton in CDCl$_3$: 7.14 ppm (d, 8H, j=7.5 Hz, Ar, H, meta) 6.80 ppm (t, 4H, J=7.5 Hz, Ar—H, para) 3.72–3.64 (m, 56H, O—C$\underline{H}_2$C$\underline{H}_2$—O+Ar—C$\underline{H}_2$—Ar)—FAB m/z=916.4.

Elementary analysis, calculated for C$_{52}$H$_{68}$O$_{14}$ C:68.10% H:7.47% —Found: C:68.30% H:7.27%.

EXAMPLE 6

Preparation of 1,3-bis(1,4 or 1,2 benzo-bis-ethylene glycol) calix[4]arenes

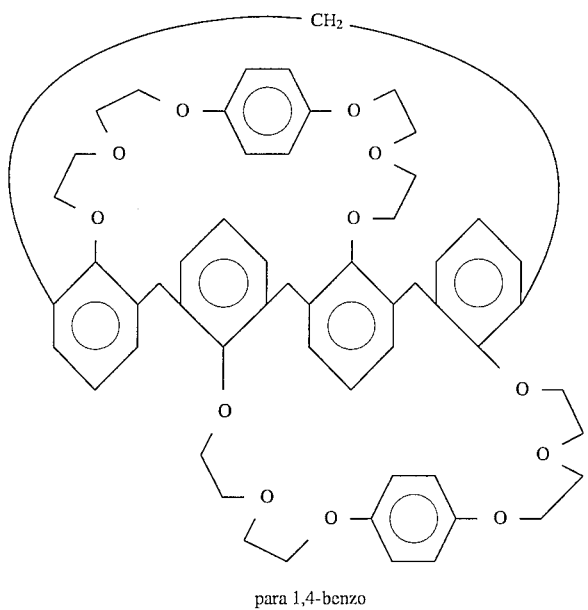

para 1,4-benzo

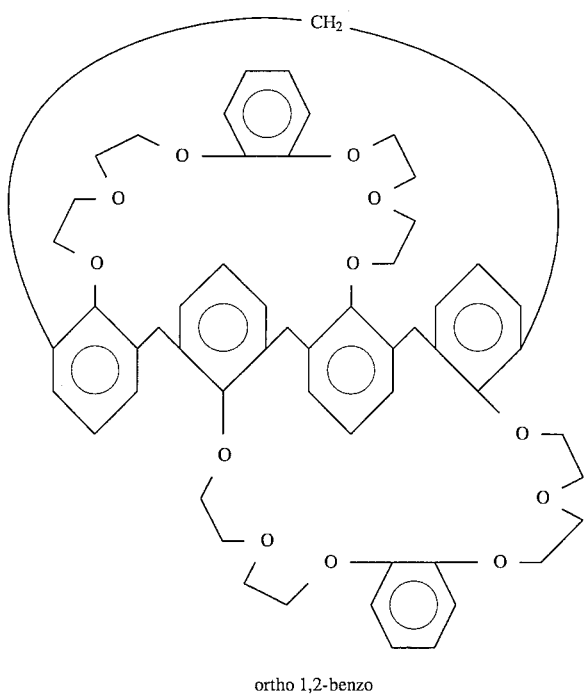

ortho 1,2-benzo a) For the para: the operating procedure of example 3 is followed for the preparation of 1,3-bis-(1,4-benzo-bis-ethylene glycol)-calix[4]arene using 1,4-bis(toluene paraethoxy ethoxy-sulphonate)-benzene in place of pentaethylene glycol-di-paratoluene sulphonate.

The "1,4-benzo" compound is obtained with a 54% yield: melting point: 81°–82° C.

NMR (CDCl$_3$) 7-07 (d, 8H, J=7.5 Hz, ArH meta) 7.03 (s, 8H, ArH, benzene) 6.83 (t, 4H, J=7.5 Hz, ArH para) 3.82–3.67 (m, 40H, —OCH$_2$ CH$_2$O—+Ar CH$_2$ Ar)

FAB m/z=924.4 b) For the ortho: the operating procedure of example 3 is followed for preparing 1,3-bis(1,2-benzo-bis-ethylene glycol)-calix[4]arene using 1,2-bis(toluene paraethoxy ethoxy-sulphonate)-benzene in place of pentaethylene glycol -di-paratoluene sulphonate. The "1,2-benzo" compound is obtained with a 62% yield:

melting point: 188°–1890 C.

NMR (CDCl$_3$)

NMR of proton in CDCl$_3$ 7.07 ppm (d, 8H, j=7.5 Hz, Ar—H, meta) 6.99 ppm (s, 8H, Ar—H catechol) 6.80 ppm (t, 4H, J=7.4 Hz, Ar—Hpara) 3.72–3.64 ppm (m, 40H, O—CH$_2$—CH$_2$ O+Ar—CH$_2$—Ar). FAB m/z=925.6.

Elementary analysis: calculated for C$_{56}$H$_{60}$O$_{12}$: C 72.70%, H 6.54%; C72.42%, H6.41%.

EXAMPLE 7 to 14

Extraction of cesium

In these examples extraction takes place of the cesium present in an aqueous solution having a nitric acid concentration of 0.97 mole/l and containing $5 \cdot 10^{-4}$ mole/l of $CsNO_3$.

For this purpose one volume of aqueous solution is contacted with one volume of organic liquid constituted by ortho-nitrophenyl hexyl ether containing $10^{-2}$ mole/l of organic extractant. When equilibrium is reached, measurement takes place by gamma spectrometry of the cesium content of the organic liquid. This is followed by the determination of the cesium percentage extracted and the distribution coefficient $D_{cs}$, which corresponds to the ratio of the cesium concentration in the organic liquid to the cesium concentration of the aqueous solution at equilibrium.

In these examples the organic extractant used is constituted by the macrocyclic ligands of Table 1, whose formulas are given in the attached drawing. The results obtained are also given in Table 1.

In these examples, example 7 to 12 relate to the use of the bis-crown calix[4]arenes according to the invention and, for comparison purposes, examples 13 and 14 illustrate the use of crown ethers as extractants.

The results of Table 1 demonstrate that the calixarene used in example 10 (caixarene of example 6b) makes it possible to obtain a very high extraction rate.

Moreover, the cesium extracted in this example can be recovered with a 77% rate by contacting the organic phase with demineralized water, the pH at equilibrium being 2.7.

EXAMPLE 15 to 20

Extraction of strontium

The starting product is an aqueous solution with a nitric acid concentration of 1.2 mole/l and containing $5 \cdot 10^{-4}$ mole/l of strontium nitrate and it undergoes extraction under the same conditions, as in examples 7 to 14 using an organic liquid phase constituted by ortho-nitrophenyl hexyl ether containing $10^{-2}$ mole/l of macrocyclic extractant.

This is followed by the measurement of the strontium content of the organic phase by gamma spectrometry and determination takes place of the extracted strontium percentage and the distribution coefficient $D_{Sr}$.

The extractants used and the results obtained are given in Table 2

EXAMPLE 21 to 27

Extraction of sodium

In these examples the starting product is an aqueous solution having a nitric acid concentraiton of 0.97 mole/l containing $5 \cdot 10^{-4}$ mole/l of sodium nitrate and it is subjected to an extraction under the same conditions as those of examples 7–14 using a macrocyclic extractant at a concentration of $10^{-2}$ mole/l in orthonitrophenyl hexyl ether. As previously, the sodium content of the organic solution is measured by gamma spectrometry and evaluation takes place of the extracted sodium percentage and the distribution coefficient $D_{Na}$.

The extractants and results obtained are given in Table 3. The results given in Tables 1 to 3 show that the bis-crown calix[4]arenes used in the invention extract cesium with good yields and separate it from the sodium and strontium present in the effluents from reprocessing plants.

On the basis of the results of Tables 1 to 3, it is possible to calculate the selectivities of the different extractants with respect to these cations in a nitric medium.

Thus, for the selectivity $\alpha(Cs/-Na)=D_{Cs}/D_{Na}$ relative to the cesium with respect to sodium the following values are obtained: 18000 for 1,3-bis(benzo 1,2-bis-ethylene glycol) calix[4]arene, 1500 for 1,3-bis-crown-6-calix[4]arene, 1250 for 1,3-bis-crown-7-calix[4]arene 200 for 1,3-bis-crown-5-calix[4]arene 126 for 1,3-bis-crown-5-O-isopropyl-calix[4] arene, whereas said selectivity is 250 for the crown ether B21C7.

For the $\alpha Cs/Sr$ selectivity relative to cesium with respect to strontium, the following values are obtained: >3000 for 1,3-bis-crown-7-calix[4]arene and 4500 for calix[4]arene-bis-crown-5, whereas this selectivity is only $7.6 \cdot 10^{-2}$ for the crown ether DCH18C6.

This is why the calixarenes according to the invention make it possible to obtain selective transports of cesium 137 in a matrix of 4M sodium nitrate and 1M nitric acid containing other fission products such as Sr 85, also in the trace state.

The results of Tables 1 to 3 also show that the 1,3-bis-crown-6-calix[4]arenes are the best extractants of cesium in the family of bis-crown calix[4]arenes. This selectivity peak could be explained by a good adequation between the size of the available cavities and the size of the extracted cation. For 1,3-bis-crown-6-calix[4]arenes, the presence of a 1,2-benzo group further improves this selectivity relative to cesium.

EXAMPLE 28 to 33

Extraction of actinides

In these examples, the starting product is an aqueous solution containing 1 mole/l of nitric acid and 4 mole/l of sodium nitrate, containing traces of Np 237, Pu 239 and Am 241 and the actinides are extracted using a liquid organic phase constituted by a macrocyclic extractant with a concentration of $10^{-2}$ mole/l in ortho-nitrophenyl octyl ether or ortho-nitrophenyl hexyl ether, or a known extractant (CMPO) at a concentration of $10^{-2}$ mole/l in orthonitrophenyl hexyl ether.

This is followed by the measurement of the Np 237, Pu 239 and Am 241 quantities present in the organic solution and determination takes place of the distribution coefficients of neptunium, plutonium and americium between the two phases in contact. The extractants used and the results obtained are given in Table 4.

These results reveal that the bis-crown calix[4]arenes of the invention are not such good extractants as CMPO, but are more selective because they do not extract trivalent americium.

Thus, it is possible to perform with 1,3-bis-crown-6-calix[4]arene transport experiments by disposing the organic liquid phase in the form of a liquid membrane separating the starting aqueous solution from a reextraction solution constituted by demineralized water, whilst decontaminating more than 95% Pu 239 and more than 50% Np 237 in less than 48 h without transporting americium.

The bis-crown calix[4]arenes according to the invention can also be used in analysis, e.g. for determining the activity of different isotopes of cesium, particularly Cs 135. They can also be used in detoxification.

TABLE 1

| Example | Organic Extractant | Cs extract (in %) | $D_{Cs}$ |
|---|---|---|---|
| 7 | 1,3-bis-crown-5-calix|4|arene (example 1) | 30 | 0.45 |
| 8 | 1,3-bis-crown-6-calix|4|arene (example 3) | 95 | 19.5 |
| 9 | 1,3-bis-(benzo-1,4-bis-ethyleneglycol) calix|4|arene (ex mple 6a) | 20 | $2 \cdot 10^{-2}$ |
| 10 | 1,3-bis-(benzo-1,2-bis-ethyleneglycol) | 97 | 31 |

TABLE 1-continued

| Example | Organic Extractant | Cs extract (in %) | $D_{Cs}$ |
|---|---|---|---|
| | calix[4]arene (ex mple 6b) | | |
| 11 | 1,3-bis-crown-7-calix[4]arene (example 5) | 23 | 0.30 |
| 12 | 1,3-bis-crown-5-p-isopropyl calix[4]arene | 10 | 0.11 |
| 13 | decylbenzo-21-(B21C7) | 24 | 0.33 |
| 14 | dicyclohexano-18-(DCH18C6) | 1.9 | $1.9 \cdot 10^{-2}$ |

TABLE 2

| Example | Organic Extractant | Sr extract (in %) | $D_{Sr}$ |
|---|---|---|---|
| 15 | 1,3-bis-crown-5-calix[4]arene (example 1) | $<10^{-2}$ | $<10^{-4}$ |
| 16 | 1,3-bis-crown-6-calix[4]arene (example 3) | 1.4 | 0.14 |
| 17 | 1-3-bis-(benzo-1,2-bis-ethyleneglycol) calix[4]arene (example 6b) | $8.5 \cdot 10^{-2}$ | $8.8 \cdot 10^{-4}$ |
| 18 | 1,3-bis-crown-7-calix[4]arene (example 5) | $<10^{-2}$ | $<10^{-4}$ |
| 19 | 1,3-bis-crown-5-p-isopropyl-calix[4]arene | $<10^{-2}$ | $<10^{-4}$ |
| 20 | dicyclohexano-18-crown-6 (DCH18C6) | 20 | 0.25 |

TABLE 3

| Example | Organic Extractant | Na extract (in %) | $D_{Na}$ |
|---|---|---|---|
| 21 | 1,3-bis-crown-5-calix[4]arene (example 1) | 0.24 | $2.3 \cdot 10^{-3}$ |
| 22 | 1,3-bis-crown-6-calix[4]arene (ex mple 3) | 1.1 | $1.3 \cdot 10^{-2}$ |
| 23 | 1,3-bis-(benzo-1,2-bis-ethyleneglycol) calix[4]arene (example 6b) | 0.17 | $17 \cdot 10^{-3}$ |
| 24 | 1,3-bis-crown-7-calix[4]arene (example 5) | $2.4 \cdot 10^{-2}$ | $2.4 \cdot 10^{-4}$ |
| 25 | 1,3-bis-crown-5-p-isopropyl calix[4]arene | $8.9 \cdot 10^{-2}$ | $8.7 \cdot 10^{-4}$ |
| 26 | decylbenzo-21-crown-7 (B21C7) | 0.13 | $1.3 \cdot 10^{-3}$ |
| 27 | dicyclohexano-18-crown-6 (DCH18C6) | 0.47 | $4.7 \cdot 10^{-3}$ |

TABLE 4

| Example | Organic Extractant | $D_{Np}237$ | $D_{Pu}239$ | $D_{Am}241$ |
|---|---|---|---|---|
| 28 | 1,3-bis-crown-5-calix[4]arene (1) (example 1) | 0.10 | 1.6 | $<10^{-4}$ |
| 29 | 1,3-bis-crown-6-calix[4]arene (1) (example 3) | 0.10 | 0.80 | $<10^{-4}$ |
| 30 | 1,3-bis-crown-5-p-iso-propyl calix[4]arene (1) | 0.11 | $9.4 \cdot 10^{-2}$ | $<10^{-4}$ |
| 31 | 1,3-bis-(benzo-1,2-bis-ethylene glycol calix[4]arene (2) (example 6b) | $5.3 \cdot 10^{-2}$ | 1.3 | $<10^{-4}$ |
| 32 | 1,3-bis-crown-7 calix[4]arene (2) (ex mple 5) | $3.1 \cdot 10^{-2}$ | 9 | $<10^{-4}$ |
| 33 | CMPO (2) | 0.85 | 22 | 1.2 |

(1) in orthonitro phenyl octyl ether: O—NPOE
(2) in orthonitro phenyl hexyl ether: O—NPHE

We claim:
1. Bis-crown calix[4]arene of formula:

(I)

in which

R¹ represents $X(C_2H_4X)_m$ with X representing O, NH and/or N (CH₃) and m being equal to 3, 4, 5 or 6, R² represents $X(C_2H_4X)_n$ with X representing O, NH and/or N(CH₃) and n being equal to 3, 4, 5 or 6, or R¹ and R² represent $X(C_2H_4X)_{p/2}YX(C_2H_4X)_{p/2}$ with X representing O, NH and/or N(CH₃), p being equal to 2 or 4 and Y representing a cyclohexylene, phenylene, naphthylene, pyridylene or thiophenylene group and R³ represents a hydrogen atom or a C₁ to C₃ alkyl group.

2. Bis-crown calix[4]arene according to claim 1, characterized in that R¹ and R² represent $O(C_2H_4O)_4$ and R³ represents a hydrogen atom.

3. Bis-crown calix[4]arene according to claim 1, characterized in that R¹ and R² represent $O(C_2H_4O)_5$ and R³ represents a hydrogen atom.

4. Bis-crown calix[4]arene according to claim 1, characterized in that R¹ and R² represent

—O(C₂H₄O)₂—⬡—O(C₂H₄O)₂— and R³ represents a hydrogen atom.

5. Process for the preparation of a bis-crown calix[4]arene according to claim 1, characterized in that it consists of reacting a calix[4]arene of formula:

(II)

in which R³ has the meaning given in claim 1,
with a tetra, penta or hexa ethylene glycol of formula:

$$HOH_2C-(CH_2OCH_2)_p-CH_2OH \quad (III)$$

in which p=2, 3, 4 or 5, or
with two different glycols of formula (III), or with a glycol of formula

[HOCH$_2$(CH$_2$OCH$_2$)$_2$]$_2$—Y  (IV)

in which Y has the meaning given in claim 1.

6. Process for the preparation of cesium from an aqueous solution, characterized in that it consists of contacting this aqueous solution with an immiscible liquid phase comprising a bis-crown calix[4]arene of formula:

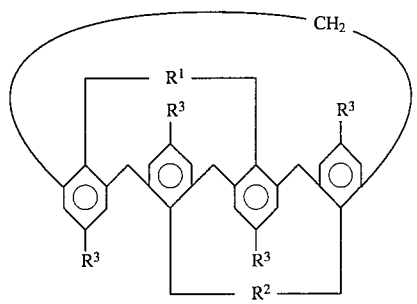 (I)

in which

R$^1$ represents X(C$_2$H$_4$X)$_m$ with X representing O, NH and/or N(CH$_3$) and m being equal to 3, 4, 5 or 6, R$^2$ represents X(C$_2$H$_4$X)$_n$ with X representing O, NH and/or N(CH$_3$) and n being equal to 3, 4, 5 or 6, or R$^1$ and R$^2$ represent X(C$_2$H$_4$X)$_{p/2}$YX(C$_2$H$_4$X)$_{p/2}$ with X representing O, NH and/or N(CH$_3$), p being equal to 2 or 4 and Y representing a cyclohexylene, phenylene, naphthylene, pyridylene or thiophenylene group and R$^3$ represents a hydrogen atom or a C$_1$ to C$_3$ alkyl group, and then recovering the cesium extracted in this liquid phase.

7. Process according to claim 6, characterized in that recovery then takes place of the cesium in an aqueous reextraction solution by contacting the liquid phase having extracted the cesium with an aqueous solution.

8. Process according to claim 7, characterized in that the aqueous reextraction solution is distilled, deionized water.

9. Process according to claim 7, characterized in that the immiscible liquid phase forms a liquid membrane and in that the aqueous solution containing the cesium is contacted with one surface of said membrane and in that the aqueous reextraction solution is contacted with the opposite surface of said liquid membrane.

10. Process according to claim 6, characterized in that the aqueous starting solution is an aqueous effluent containing cesium, with or without sodium and/or strontium, obtained from an irradiated fuel reprocessing installation.

11. Process for separating actinides and trivalent americium present in an aqueous solution, characterized in that it consists of contacting said aqueous solution with an immiscible liquid phase comprising a bis-crown calix[4]arene according to claim 1 and then recovering the extracted actinides in the immiscible liquid phase.

* * * * *